United States Patent [19]
Yufa

[11] Patent Number: 5,946,091
[45] Date of Patent: Aug. 31, 1999

[54] METHOD AND DEVICE FOR PRECISE COUNTING AND MEASURING THE PARTICLES

[76] Inventor: Aleksandr L. Yufa, P.O. Box 1677, Colton, Calif. 92324

[21] Appl. No.: 08/843,648

[22] Filed: Apr. 10, 1997

[51] Int. Cl.⁶ .................................................. G01N 15/02
[52] U.S. Cl. ........................................... 356/336; 356/339
[58] Field of Search .................................. 356/335–343, 356/244, 246, 440, 441, 442; 250/574, 576, 564

[56] References Cited

U.S. PATENT DOCUMENTS 3,632,210  1/1972  Rich ........................................ 356/338
5,471,299  11/1995  Kaye et al. .............................. 356/336
5,600,438  2/1997  Kreikebaum et al. ................... 356/246

*Primary Examiner*—Hoa Q. Pham

[57] ABSTRACT

A device provides a precise counting and measuring the particles and includes a capillary particle flow system, comprising at least one of a plurality of capillary particle flow channels, the axes of which intersect each other and a light beam at a point, belonging to the focus of the particle detecting system. Each capillary particle flow channel is intended for the passage of the predetermined size particles. A device also includes the synchronously operating blower and purger, the inlet and outlet filters, a control system, and the extended inlet and outlet particle flow tubular systems, the valves, providing a synchronous connection of the appropriate capillary particle flow channels to the inlet and outlet executive systems.

11 Claims, 14 Drawing Sheets

METHOD AND DEVICE FOR PRECISE COUNTING AND MEASURING THE PARTICLES

FIELD OF THE INVENTION

This invention relates to the air and liquid quality and, more particularly, to devices and instruments for particle quantity counting and particle size measuring by laser or light beam.

BACKGROUND OF THE INVENTION

The methods and devices for determining quantity and size of the particles and small bodies are now well known, and it is also well known that powerful light or laser and optical system or mirror can be, and have been, heretofore used to achieve particle size and particle quantity measurements. Such devices using light scattering are well known and described in the articles: R. G. Knollenberg, B. Schuster—"Detection and Sizing of Small Particles in Open Cavity Gas Laser," Applied Optics, Vo.11, No.7, November 1972, pp.1515–1520; R. G. Knollenberg—"An Active Scattering Aerosol Spectrometer," Atmospheric Technology, No.2, June 1973, pp.80–81; R. G. Knollenberg—"Active Scattering Aerosol Spectrometry," National Bureau of Standards Special Publication, No.412, October 1974, pp.57–64; R. G. Knollenberg, R. E. Luehr—"Open Cavity Laser Active Scattering Particle Spectrometry from 0.05 to 5.0 Microns," Fine Particles, Aerosol Generation Measurement, Sampling and Analysis, Academic Press, May 1975, pp.669–696; R. G. Knollenberg—"Three New Instruments for Cloud Physics Measurements: The 2-D Spectrometer, the Forward Scattering Spectrometer Probe, and the Active Scattering Aerosol Spectrometer", American Meteorological Society, International Conference on Cloud Physics, July 1976, pp. 554–561; R. G. Knollenberg—"The Use of Low Power Laser in Particle Size Spectrometry", Proceeding of the Society of Photo-Optical Instrumentation Engineers, Practical Applications of Low Power Lasers, Vo.92, August 1976, pp.137–152; R. G. Knollenberg—"The Measurement of Particle Sizes Below 0.1 Micrometers", Journal of Environment Science, January–February, 1985, pp. 64–67.

The reference in these articles is made to the devices and methods of particulate measurement utilizing an open cavity laser. These methods and devices use the imaging systems which are based on lens use, the same as it mentioned, for example, in the U.S. Pat. No. 4,798,465 and in the U.S. Pat. No. 4,140,395 of the prior art.

The other devices mentioned in prior art (for example, U.S. Pat. No. 4,606,636) use a non-divergent quadric reflector. These devices use a paraboloidal sphere as mirror.

Yet in other prior art (for example, such as U.S. Pat. No. 4,523,841 and U.S. Pat. No. 5,467,189) we can find the devices (the sensors) with the elliptical mirrors instead the lens systems or the non-divergent mirrors.

All these devices, mentioned in the prior art above, use very narrow light (laser) beam, but not consider the width of the particles flow. It means that just particles which intersect the narrow light beam at the focal point (focus) are considered for counting and measuring processes. As shown on FIG. 1, the scattered light related to non-focused particles, mentioned of the above, will be stochastically reflected (the scattered light will be not directed to the second focal point 9 of the mirror system 4, where is located a light detection means 5). It is understood that the scattered light related with the particles, which will not pass through the focus 8, create the non-focused scattered light 7, which will not be detected by light detection means 5.

The counting and measuring device (sensor) by U.S. Pat. No. 5,515,164 uses increased cross-sectional size of the particle flow. On FIG. 2 is shown the part of the sensor which has specially increased cross-sectional area of the particle flow exit mouth 72, extended along the light beam axis 2. FIG. 2 also presents some configurations (forms) of the particle flow exit mouth 72, according to mentioned U.S. Pat. No. 5,515,164. Such devices provide counting and measuring only minimal portion of assaying air, because only particles of the particle flow, which pass through the point of the intersection with very narrow light beam and exactly at the focal point 8 (first focus) will creat a focused scattered light 6 and will be detected by light detection means 5. All other particles of the particle flow can not be counted, measured and relative non-focused scattered light 7 will create highest background (light noises).

Also the turbulence, used in mentioned above device creates the air-eddying movements, which can lift already counted and measured particles for frequentative counting and measuring, thereby creating incorrectness of the resulting information.

The same regards to the devices, referring to mentioned above U.S. Pat. No. 4,798,465 and No. 4,140,395, which use the optical systems 11 (for example, lenses). As we can see from FIG. 3, the non-focused scattered light 7 will be undetected and thereby will also create the light noises, as was mentioned for the device, using mirrors.

On FIG. 4 is presented the device, using non-divergent quadric mirror, regarding U.S. Pat. No. 4,606,636. From FIG. 4 we see that the non-focused scattered light 7 creates the light noises too.

Everything described of the above can be applied to the liquid particle (contaminations) counters, using uninterrupted (undivided) liquid flow trace instead divided particle flow trace, as it was mentioned for airborne particle counting and measuring devises.

Some information about a prior art method and devices can be also obtained from: Peters—"20 Good Reasons to Use In Situ Particle Monitors", Semiconductor International, November 1992, pp.52–57; Busselman et al.—"In Situ Particle Monitoring in a Single Wafer Poly Silicon and Silicon Nitride Etch System", IEEE/SEMI Int'l Semiconductor Manufacturing Science Symposium, 1993, pp.20–26 and U.S. Pat. No. 5,083,865 (Feb. 28, 1992).

It is known, that integrated circuits (chips) and semiconductors have been produced in "clean rooms". The air in such "clean rooms" should be very well cleaned. The continuing tendencies of the improvement of circuit integration and degree of microminiaturization require corresponding improvements of the environment in "clean rooms" and efficiency of the measuring devices. And now, as known from prior art, the sensitivity of the counting and measuring devices should be at least as small as 0.1 Micron.

Thus, the non-focused scattered light in the mentioned above devices of a prior art creates the light background (light noises) inside the sensor, creating incorrectness of resulting information about outside environment and additionally light noise limits the sensitivity of such devices.

OBJECT AND ADVANTAGES OF THE INVENTION

Accordingly, several objects and advantages of the present invention are to provide an improved method and device for counting and measuring the particles.

It is another object of the invention to provide an improved method and device for increasing the precision of particles counting and measuring.

It is still another object of the invention to provide an improved method and device for increasing the efficiency of the measuring and counting process result.

It is still further object of the invention to provide an improved method and device for increasing the authenticity of the information about air or liquid composition.

It is yet another object of the invention to provide an improved method and device to decrease light noises by eliminating non-focused scattered light background inside an improved device.

It is yet further object of the invention to provide an improved method and device capable of providing high sensitivity.

It is another further object of the invention to provide an improved method and device that eliminates light noises (background noises) due to molecular scattering to a level that allows counting and measuring of particulate sizes at least as small as 0.1 Micron ($\mu$m) in high molecular scattering environments.

Still, further objects and advantages will become apparent from a consideration of the ensuing description accompanying drawings.

SUMMARY OF THE INVENTION

This invention provides a method and device having a high sensitivity and a precision of counting and measuring particles, wherein a particle size sensitivity achieves of at least as small as 0.1 $\mu$m. An improved method of counting and measuring the particles forms a particle flow system, wherein the non-focused scattered light is eliminated. For this purpose an assaying particle flow passes in the formed capillary particle flow system through at least one of a plurality of capillary particle flow means, each axis of which intersects a light beam at a point of a particle detecting system focus.

Each apart of N=1, 2, ..., i, ..., m capillary particle flow means has inside diameter intended for passing the particles, which are not bigger than a priori determinate (predetermined) particle size.

By an improved method, an improved device detects the particles, for example, by light scattering, which is occurred inside particle detecting system at a point of a first focus of particle detecting system by an intersection of a light beam with the particles of assaying particle flow. The detection means is placed at the second focus of the particle detecting system (the particle detecting system, using the direct detection principles, can have one focus at the point of the light beam and particle flow intersection).

An improved device compresses a capillary particle flow system, a particle detecting system, a control system, a valved means, a blowing and purging means, a inlet and outlet filtrating means, an extended particle flow tubular means.

The valved means provides the switching and non-leaking, tight connection of the one of N=1, 2, ..., i, ..., m particle flow channels to the particle detecting system and to appropriate means of the improved device.

DESCRIPTION OF THE PREFERRED EMBODIMENTS

Here the description of an improved method and device will be done in statics (as if the components of the improved device are suspended in the space) with description of their relative locations and connections each other. The description of the improved processes and functional operations of an improved device will be done hereafter.

Figure 1:
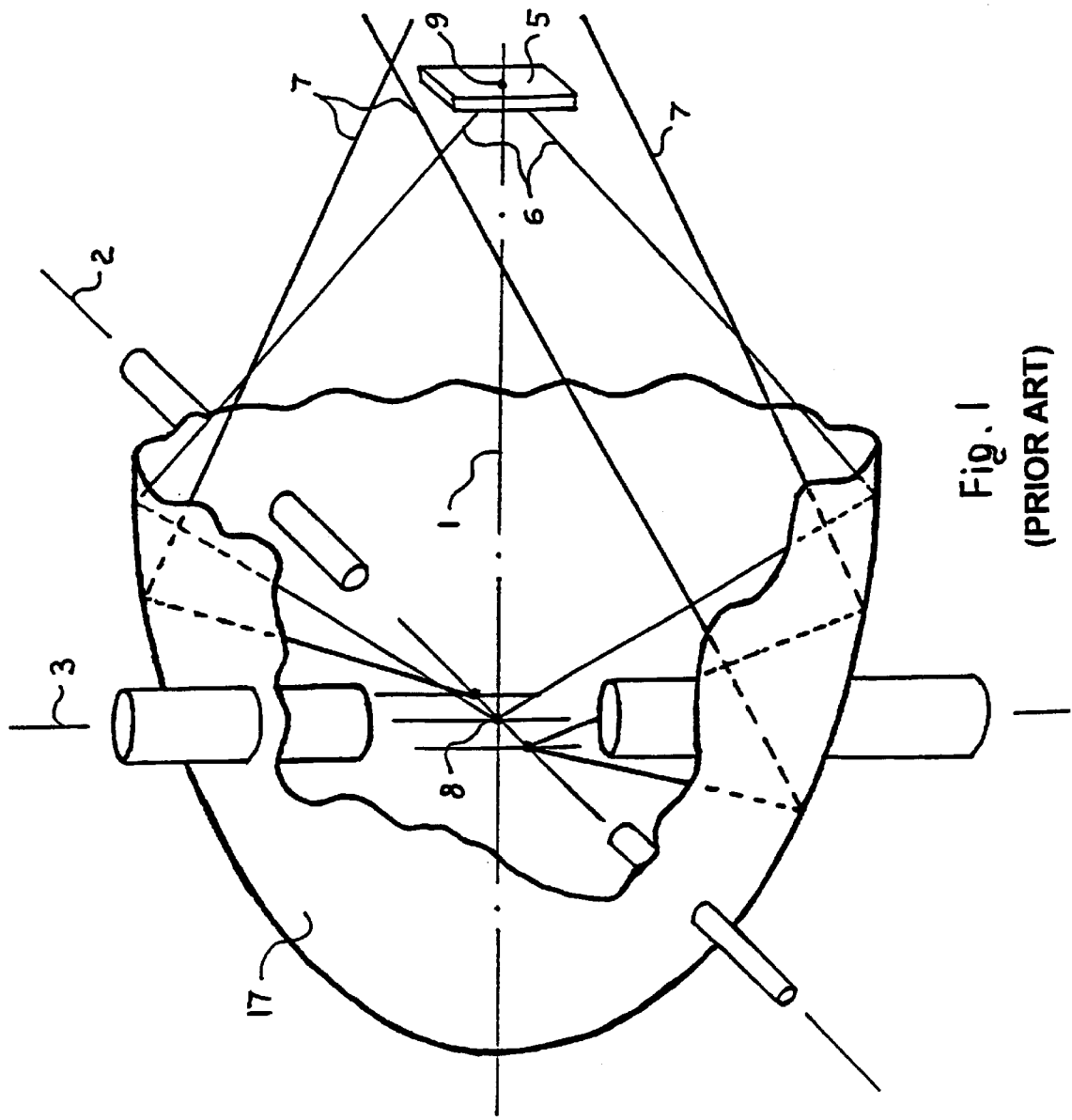
FIG. 1 is a deficiency of the non-focused scattered light distribution in the prior art devises (sensors) with elliptical mirrors.
Figure 2:
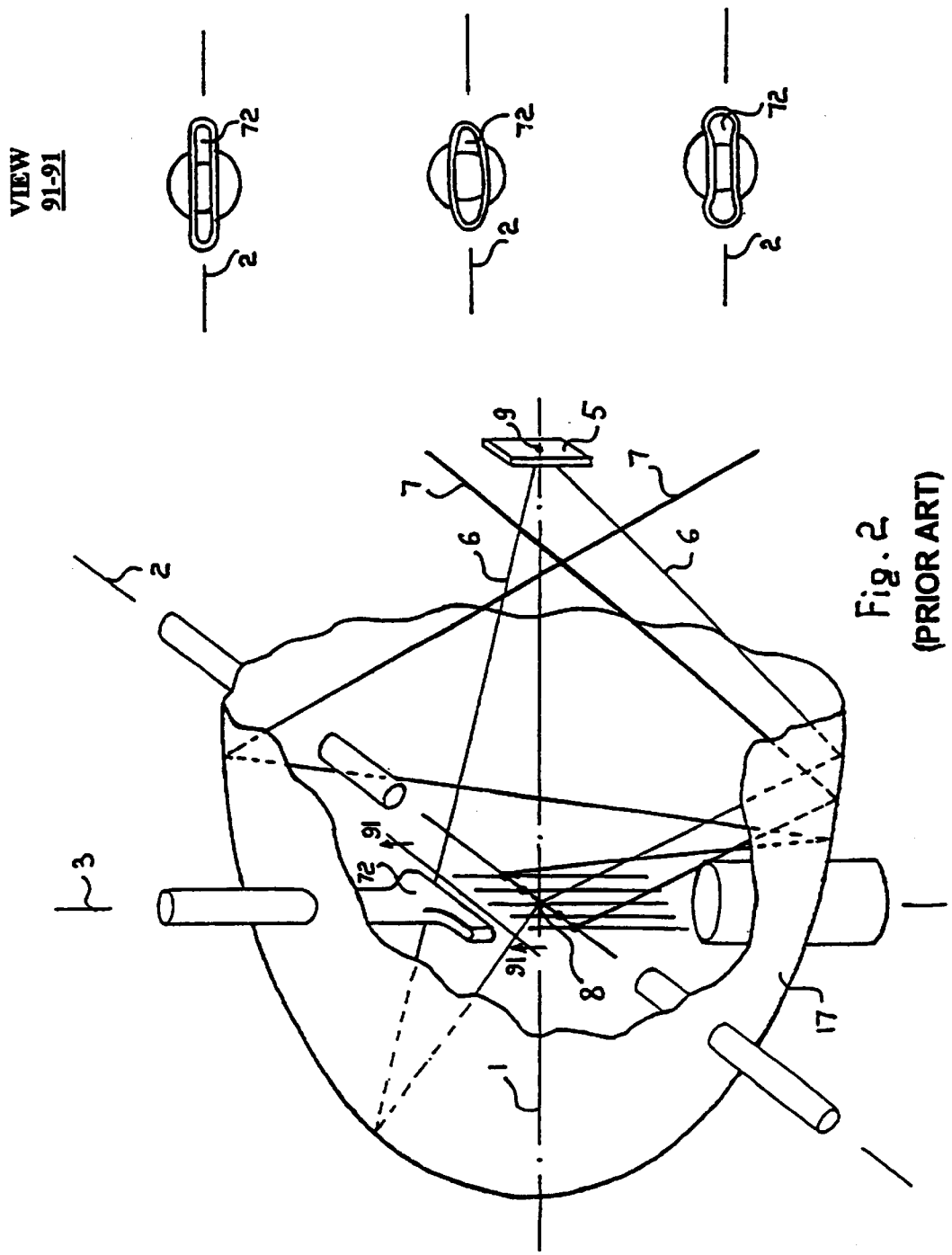
FIG. 2 is a simplified drawing of the prior art particle flow exit mouth configuration.
Figure 3:
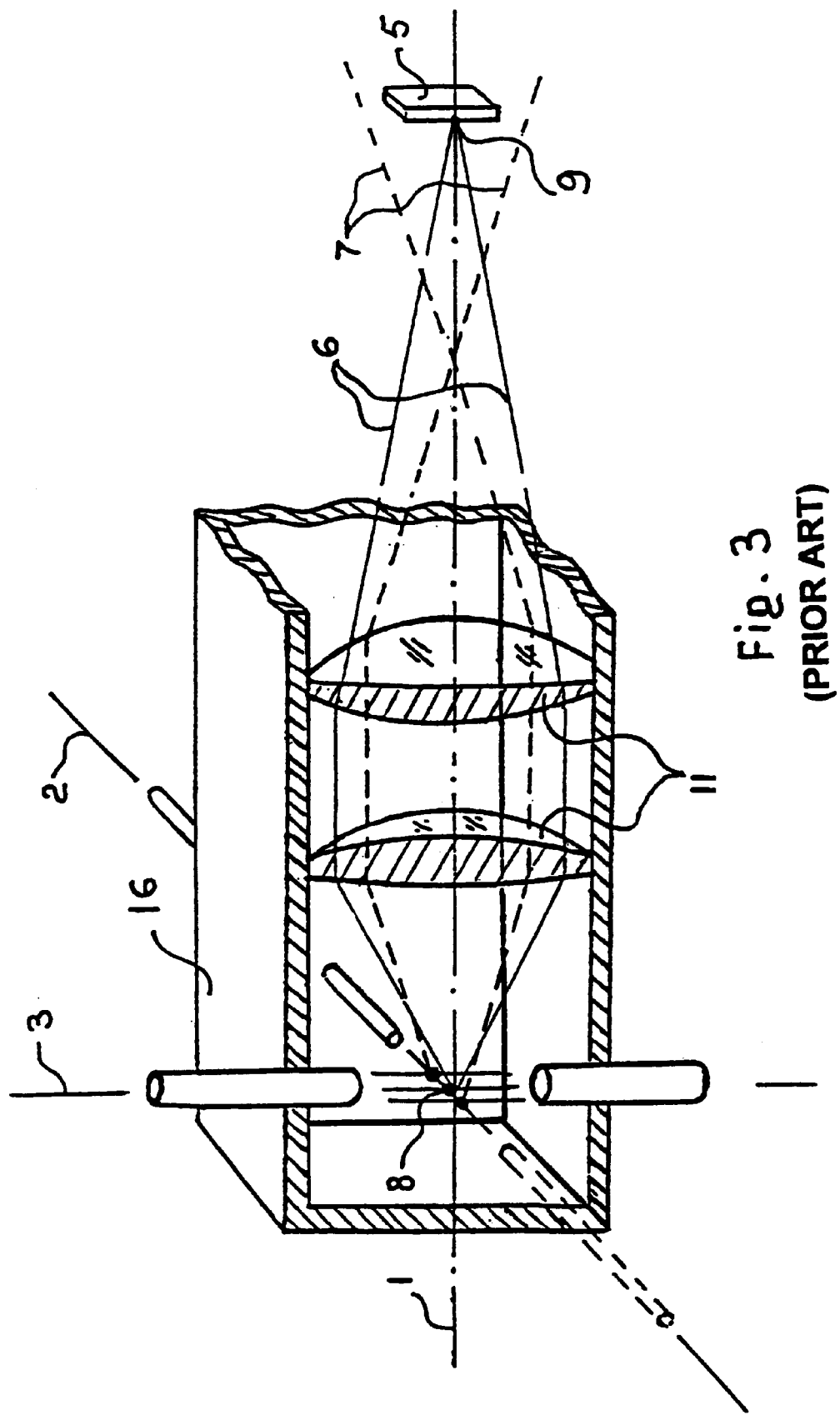
FIG. 3 is a deficiency of the non-focused scattered light distribution in the prior art devices (sensors) with optics.
Figure 4:
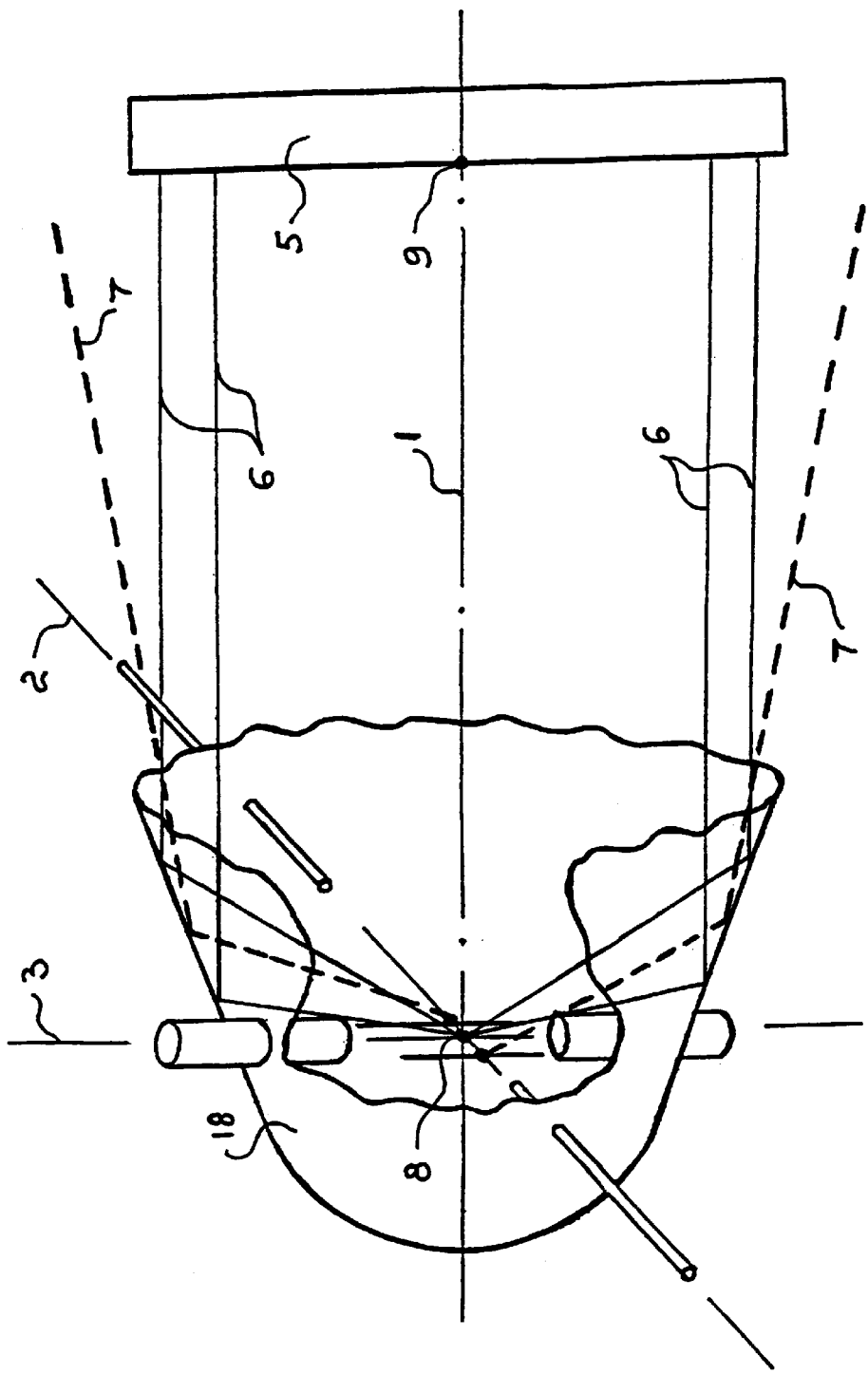
FIG. 4 is a deficiency of the non-focused scattered light distribution in the prior art devices (sensors) with non-divergent quadric mirrors.
Figure 5:
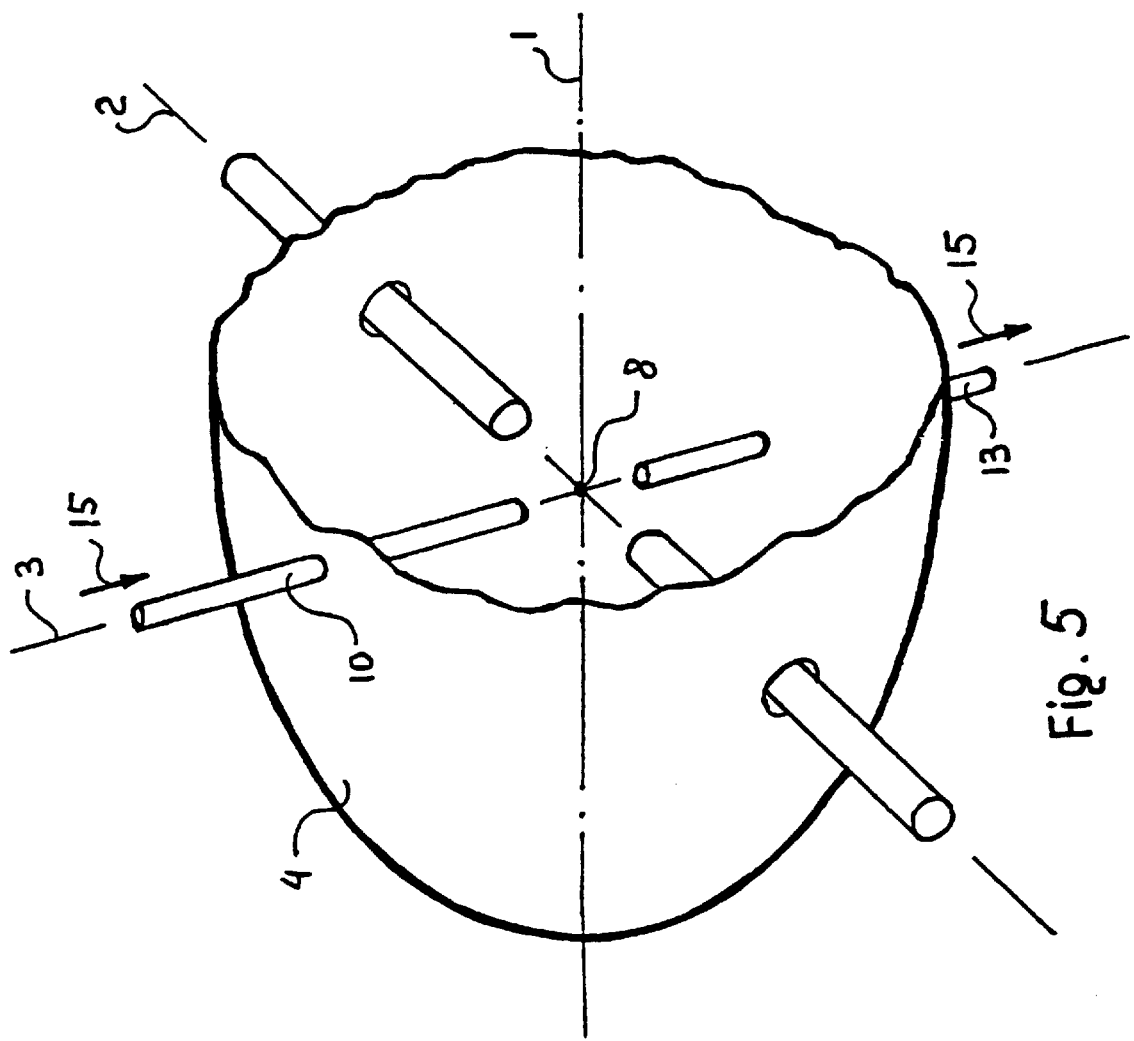
FIG. 5 is an isometric spatial simplified representation of certain aspects of an improved method and one channel improved device.

An improved device, referring to FIG. 5, includes a device axis 1, a light beam (for example, a powerful light beam or can be used a laser beam) along axis 2, a particles flow along axis 3, intersecting the light beam on the device axis 1 at the first focus 8 of the mirror system 4. The mirror system 4 hereby represents the use of a non-divergent quadric mirror or an ellipsoidal mirror or an ellipsoidal mirror system (the second focus, wherein on a device axis 1 is placed a light detection means, is not shown). The particle detecting system, using the direct detection principles, is not shown. Also an improved device includes a capillary inlet particle flow means 10, placed along axis 3 and connected to the mirror system 4 and further through mirror system 4 also connected to an extended entrance particle flow tubular means 12, a capillary outlet particle flow means 13, placed also along axis 3 and connected to the mirror system 4 and further through the mirror system 4 connected to the relative extended exit particle flow tubular means 14. The inside diameter "d" of a capillary inlet particle flow means 10 (see FIG. 10) is related to the counting and measuring a priori determinated particle size only:

$$d = S|^{+T} \qquad [1]$$

where d—an inside diameter of the capillary inlet particle flow means;

S—a particle size, intended for counting and measuring;
T—a tolerance:

$$T = f(S) \quad [2]$$

where
$f$—a functional symbol (a function).

For example, if it is necessary to count and measure the particles with S=0.1 μm, the inside diameter "d" of the capillary inlet particle flow means 10 can be, for instance: 0.12 μm≦d≦0.15 μm(where "T" is: $T_{min} \leq T \leq T_{max}$ and $T_{min}=-0.02$ μm, $T_{max}=+0.05$ μm). The value of $T_{min}$ is determined by unobstructed particle passing inside a capillary inlet particle flow means 10 and the value of $T_{max}$ is determined by elimination of two particles side-by-side passage (beside each other along axis 1 or axis 2) at the same time.

For counting and measuring liquid contaminations (particles), a liquid flow means can have the undivided capillary liquid flow means inside mirror or mirror system or inside the chamber of the optical system or direct detecting system. The capillary liquid flow means can be divided (broken) in the focal area, if the special liquid chamber will be used and placed in the mentioned focal area. The inside diameter of the capillary liquid flow means is also determined by the particle size in accordance with the equations [1] and [2].

For providing of the multi purposes (precise counting and measuring the particles of the different sizes) an improved device includes a capillary particle flow system, comprising N=1, 2, . . . , i, . . . , m particle flow (means channels), each of which has a capillary inlet particle flow means and an appropriate capillary outlet particle flow means. The axis of each capillary inlet particle flow means and the axis of an appropriate capillary outlet particle flow means are coincident (are placed along the same axis). For an improved device, presented on FIG. 5, a capillary particle flow system has one particle flow channel (single capillary particle flow means),for which N=1.

Figure 6:
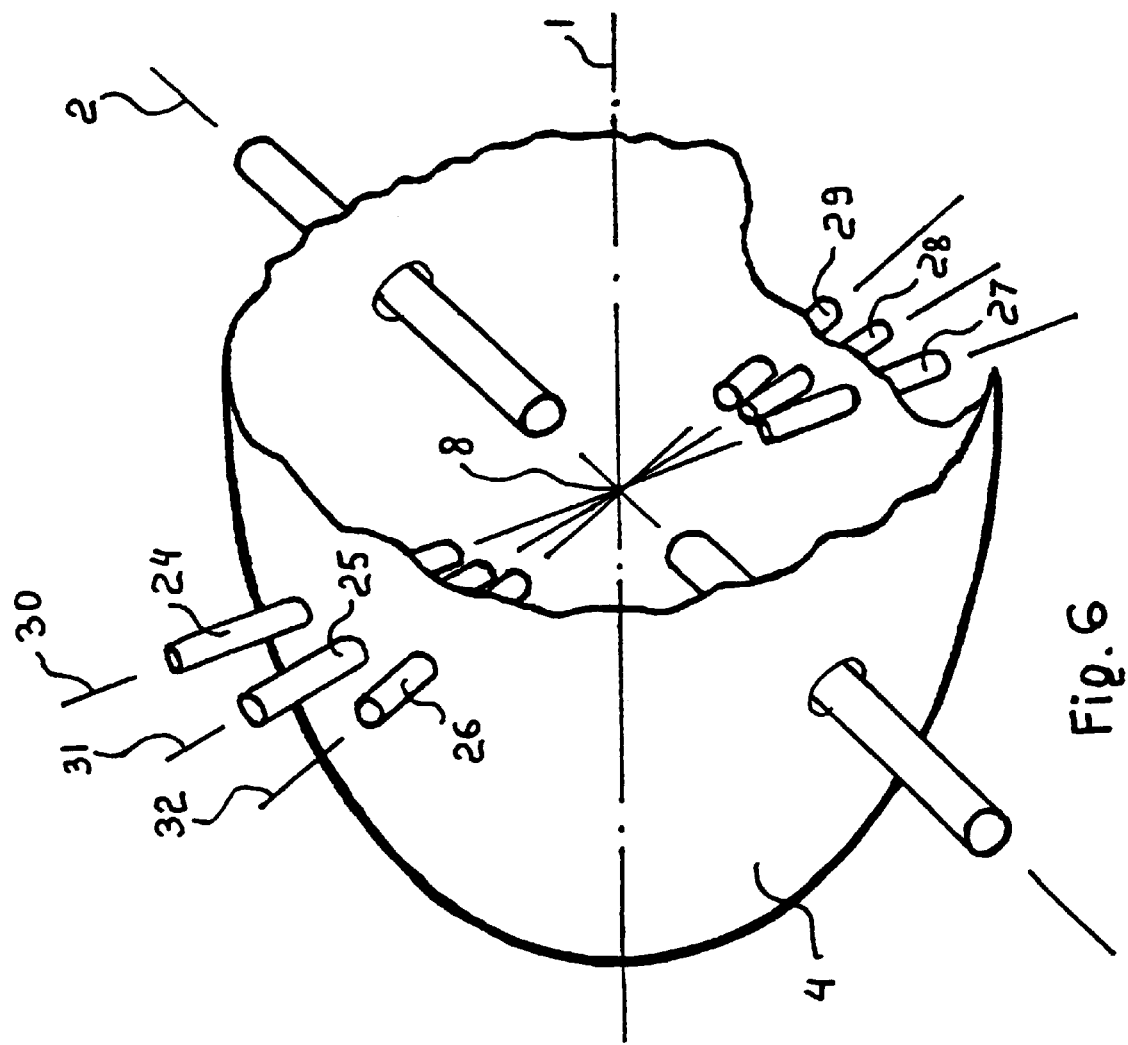
FIG. 6 is a simplified isometric spatial representation of the certain aspects of an improved method and the first variant of the multi channels improved device.

On FIG. 6 is presented an improved device, having, as example, three (N=3) particle flow channels, each axis 30, 31, 32 of which intersects the light beam axis 2 at the first focus 8 on a device axis 1. A channel 30 includes a capillary inlet particle flow means 24 and appropriate capillary outlet particle flow means 27, a channel 31 includes a capillary inlet particle flow means 25 and appropriate capillary outlet particle flow means 28, and a channel 32 includes a capillary inlet particle flow means 26 and appropriate capillary outlet particle flow means 29. The capillary inlet particle flow means 24, 25, 26 are connected to the appropriate extended inlet particle flow tubular means 34, 35, 36, which are connected to an extended entrance particle flow tubular means 12 by controllable (handle or electronic) inlet valved means 33 of the valved means 74 (see FIG. 12) and the capillary outlet particle flow means 27, 28, 29 are connected to the appropriate extended outlet particle flow tubular means 37, 38, 39, which are connected to an extended exit particle flow tubular means 14 by controllable (handle or electronic) outlet valved means 44 of the valved means 74 (see also FIG. 12).

Figure 9:
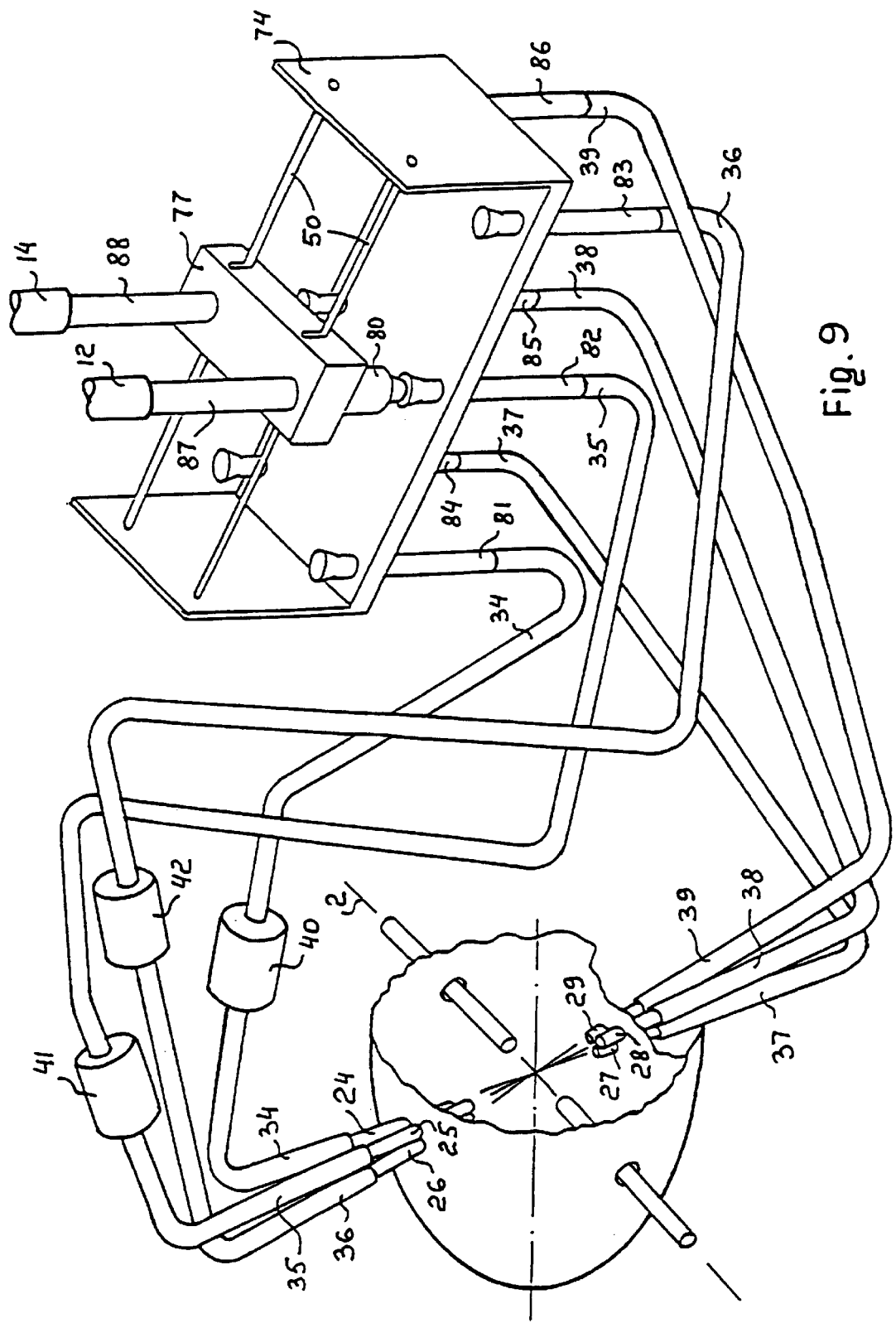
FIG. 9 is a simplified drawing of the certain aspects tubular connections.

On FIG. 9 is shown the simplified tubular connection of a capillary particle flow means to the valved means 74 and also the connection of the extended entrance 12 and extended exit 14 particle flow tubular means to the appropriate inlet 87 and outlet 88 particle flow tubular means of the valved means 74.

The inlet filters 40, 41, 42 are "cut in" (are housed in) the appropriate extended inlet particle flow tubular means 34, 35, 36. The extended outlet particle flow tubular means 37, 38, 39 are directly connected to the valved means 74.

Figure 7:
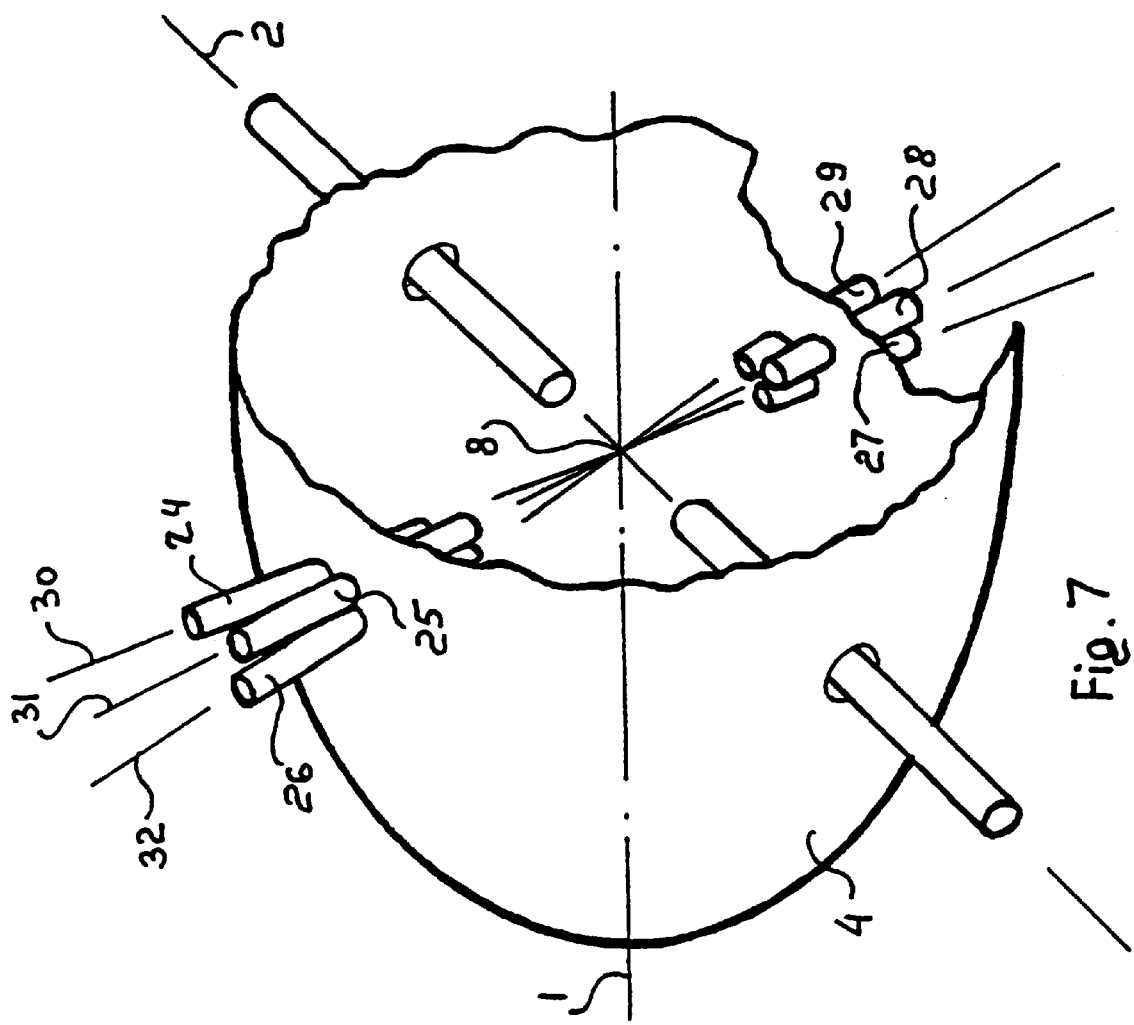
FIG. 7 is a simplified isometric spatial representation of the certain aspects of an improved method and the second variant of the multi channel improved device.

The FIG. 7 represents the another possible variant of the capillary particle flow means housing into mirror system 4. Considering the housing of the capillary inlet particle flow means 24, 25, 26, presented on FIG. 7, the capillary outlet particle flow means 27, 28, 29 can be substituted for an outlet particle flow means 43, according to FIG. 8.

Figure 8:
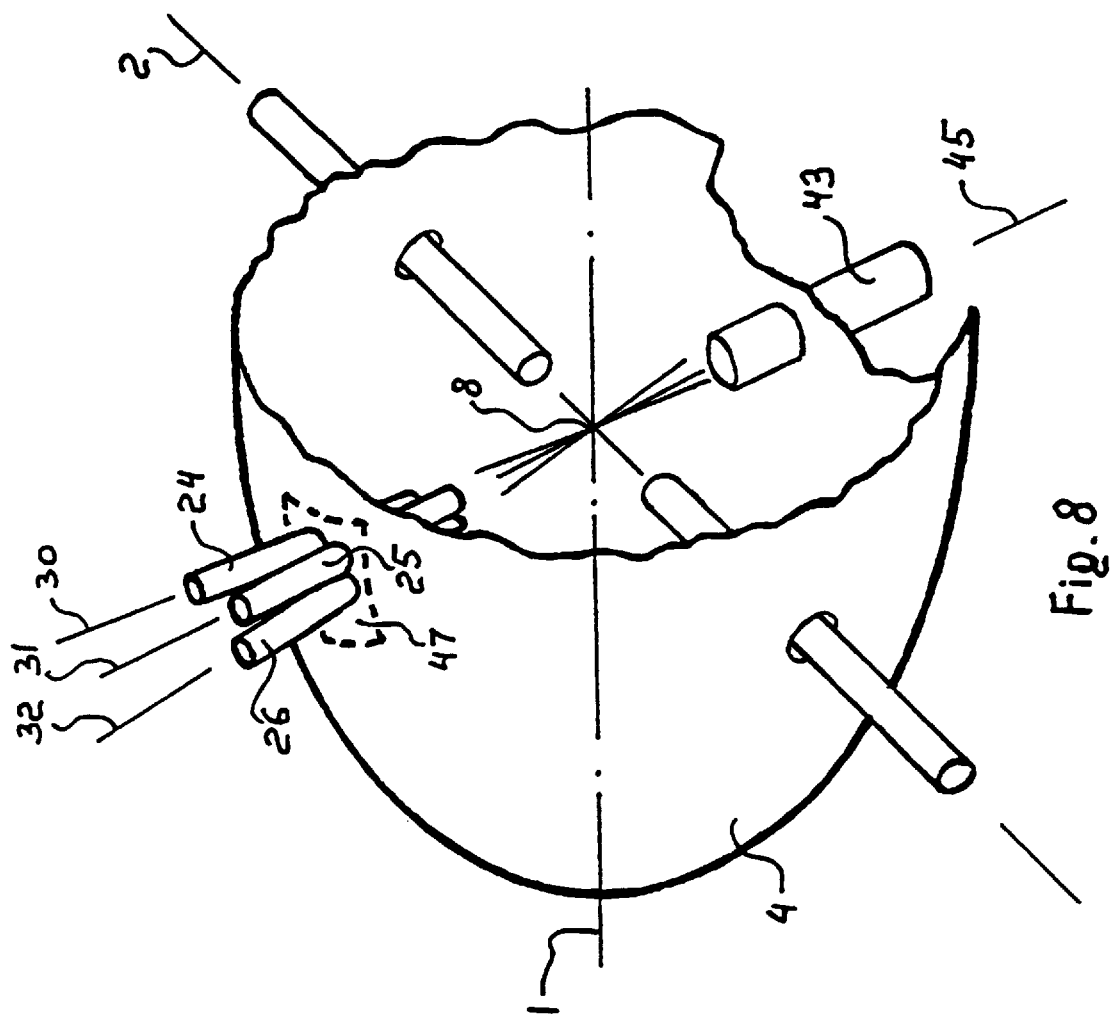
FIG. 8 is a simplified isometric spatial representation of the certain aspects of an improved method and the third variant of the multi channels improved device.

Concerning FIG. 8, the outlet particle flow means axis 45 is directed through first focus 8 to the surface 47 perpendicularly. A surface 47 is a portion of an mirror surface, limited by area of the N=1, 2, . . . , i, . . . , m capillary inlet particle flow means connection to the mirror system 4. Considering substitution, mentioned above, the outlet particle flow means 43 will connect to the extended exit particle flow tubular means 14 directly.

Figure 10:
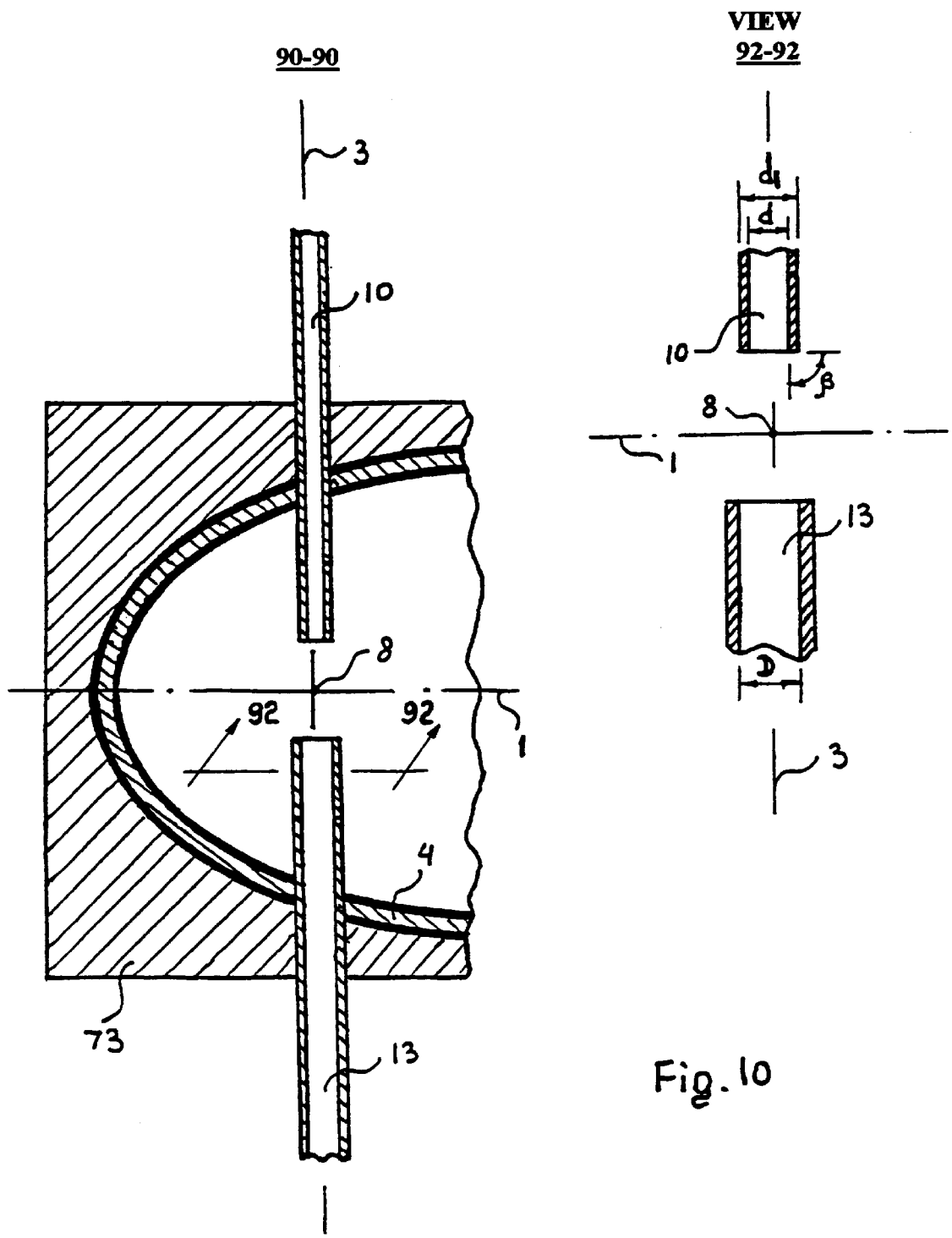
FIG. 10 is a cross-sectional simplified drawing of an improved device taken from the perspective of viewing axes 90—90 of FIG. 5, including simplified housing of the components.

On FIG. 10 is shown simplified housing the means inside a chamber 73 and also possible correlation of the capillary inlet particle flow means dimensions and the capillary outlet particle flow means dimensions, considering of the above, referred to FIGS. 5–7. As shown on FIG. 10, the inside diameter of the i-th capillary outlet particle flow means $D^{(i)}$ is adequate to outside diameter $d_l^{(i)}$ of a capillary inlet particle flow means $\{D^{(i)}=d^{(i)}_l\}$ and the angle $\beta=90°$ is preferable.

Figure 11:
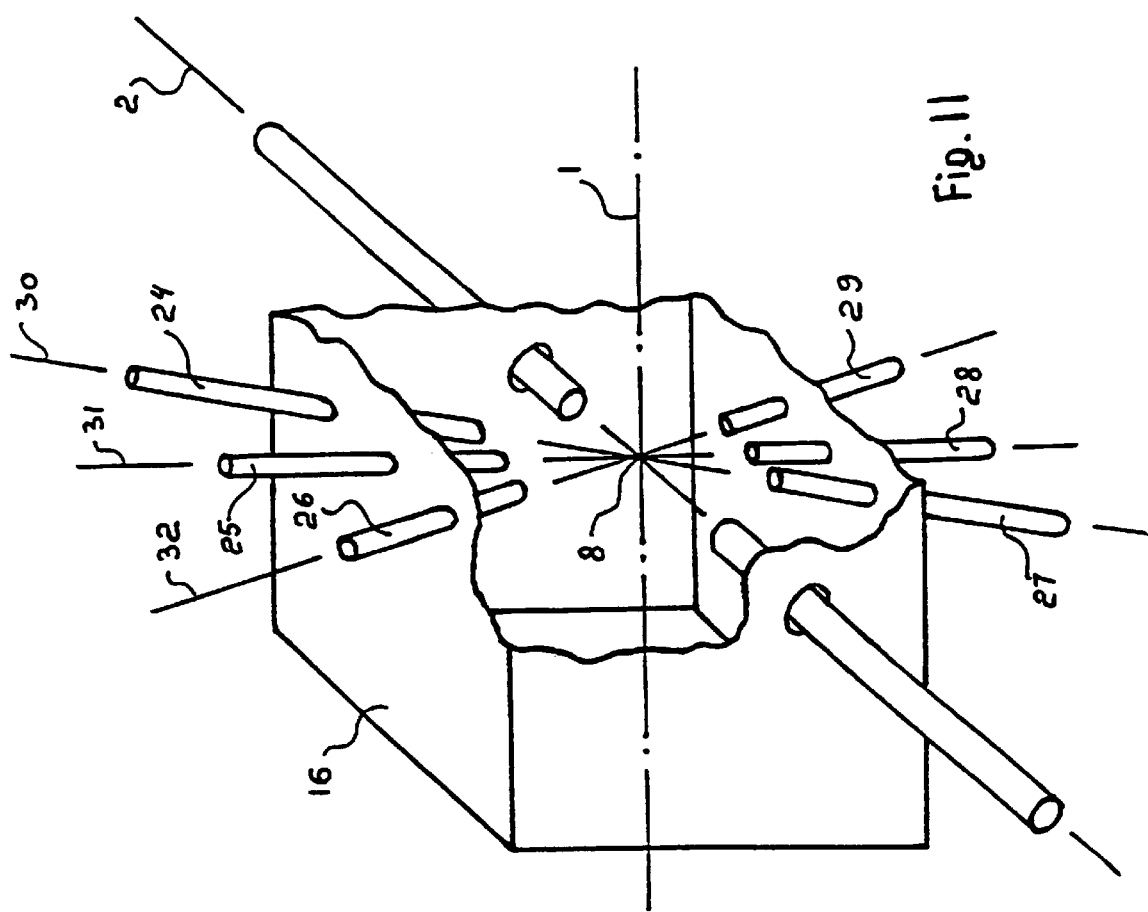
FIG. 11 is a simplified drawing of the third variant of an improved device, using an optical system.

FIG. 11 illustrates the described of the above principles, applied to the optical system. On FIG. 11, as example, are shown one variant of the capillary particle flow system housing. The geometric configuration of the chamber 16 can also be, for example, cylindrical, etc.

Figure 12:
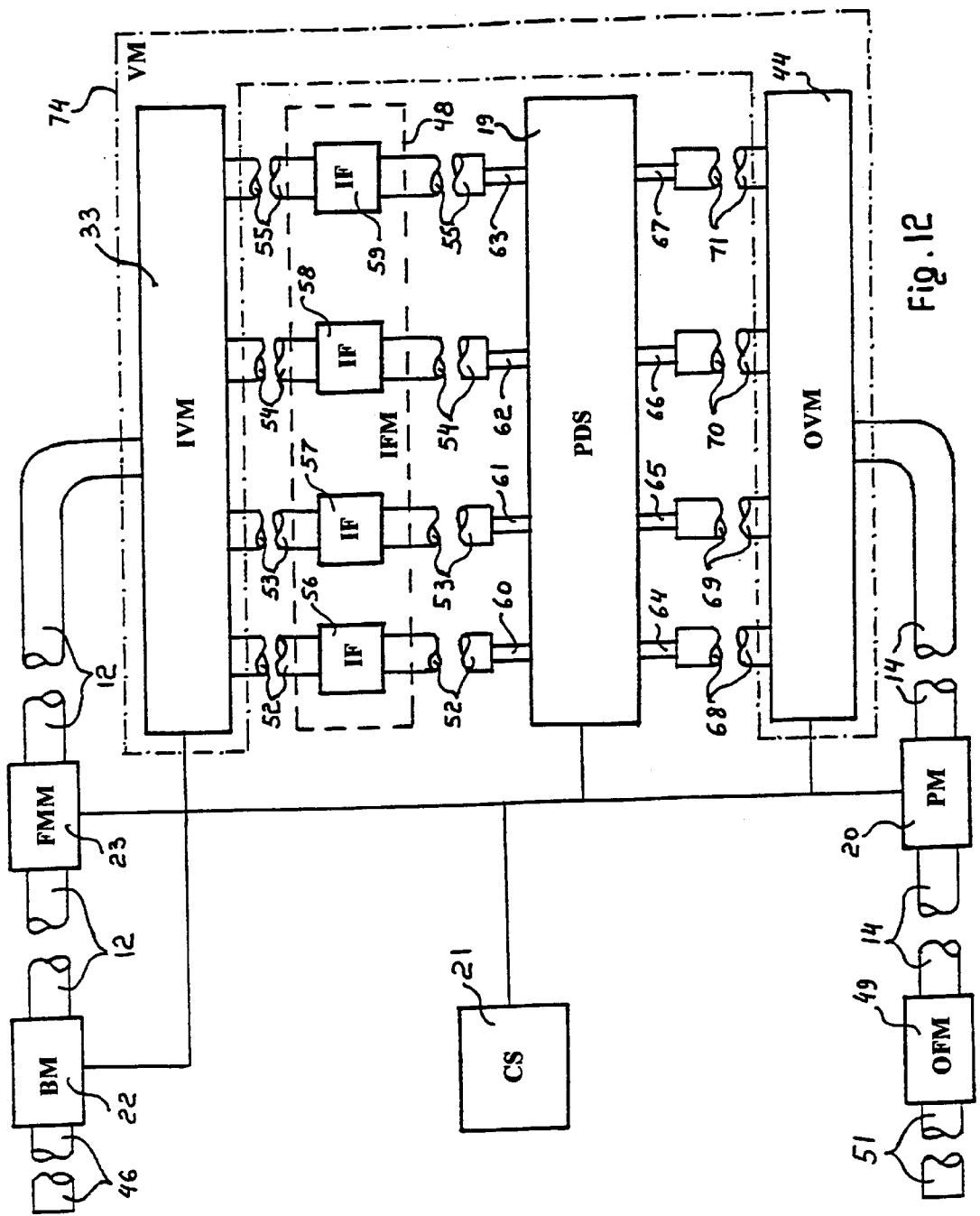
FIG. 12 is a simplified kinematic schematic (block-diagram) of an improved device.

FIG. 12 represents block diagram of an improved device. Referring to FIG. 12, the improved devise comprises an entrance particle flow tubular means 46 is connected by an extended entrance particle flow tubular means 12 through a blowing means 22 and flow measuring means 23 to an inlet valved means 33 of the valved means 74. The inlet valved means 33 by N=1, 2, . . . , i, . . . , m extended inlet particle flow tubular means (on FIG. 12 are presented as 52–55) is connected through appropriate N=1, 2, , . . . , i, . . . m filters (on FIG. 12 are presented as 56–59) of the inlet filtrating means 48 to the appropriate N=1, 2, . . . , i, . . . , m capillary inlet particle flow means, which are presented on FIG. 12 as 60–63. The particle detecting system 19 comprises a source of a light beam (not shown on FIG. 12), a light detection means (not shown) and a mirror or a mirror system or an optical system (not sown on FIG. 12), including means described of the above, concerning FIGS. 5–11. The N=1, 2, . . . , i, m capillary outlet particle flow means (on FIG. 12 are presented as 64–67) are connected by N=1, 2, . . . , i, . . . m extended outlet particle flow tubular means (on FIG. 12 are presented as 68–71) to an outlet valved means 44 of valved means 74, which by an extended exit particle flow tubular means 14 is connected to a purging means 20. The purging means 20 through outlet filtration means 49 and exit particle flow tubular means 51 is connected to the outside environment.

Also referring to FIG. 12, a blowing means 22, a flow measuring means 23, an inlet valved means 33 of the valved means 74, a particle detecting system 19, an outlet valved means 44 of the valved means 74 and a purging means 20 are connected to a control system 21.

Figure 13:
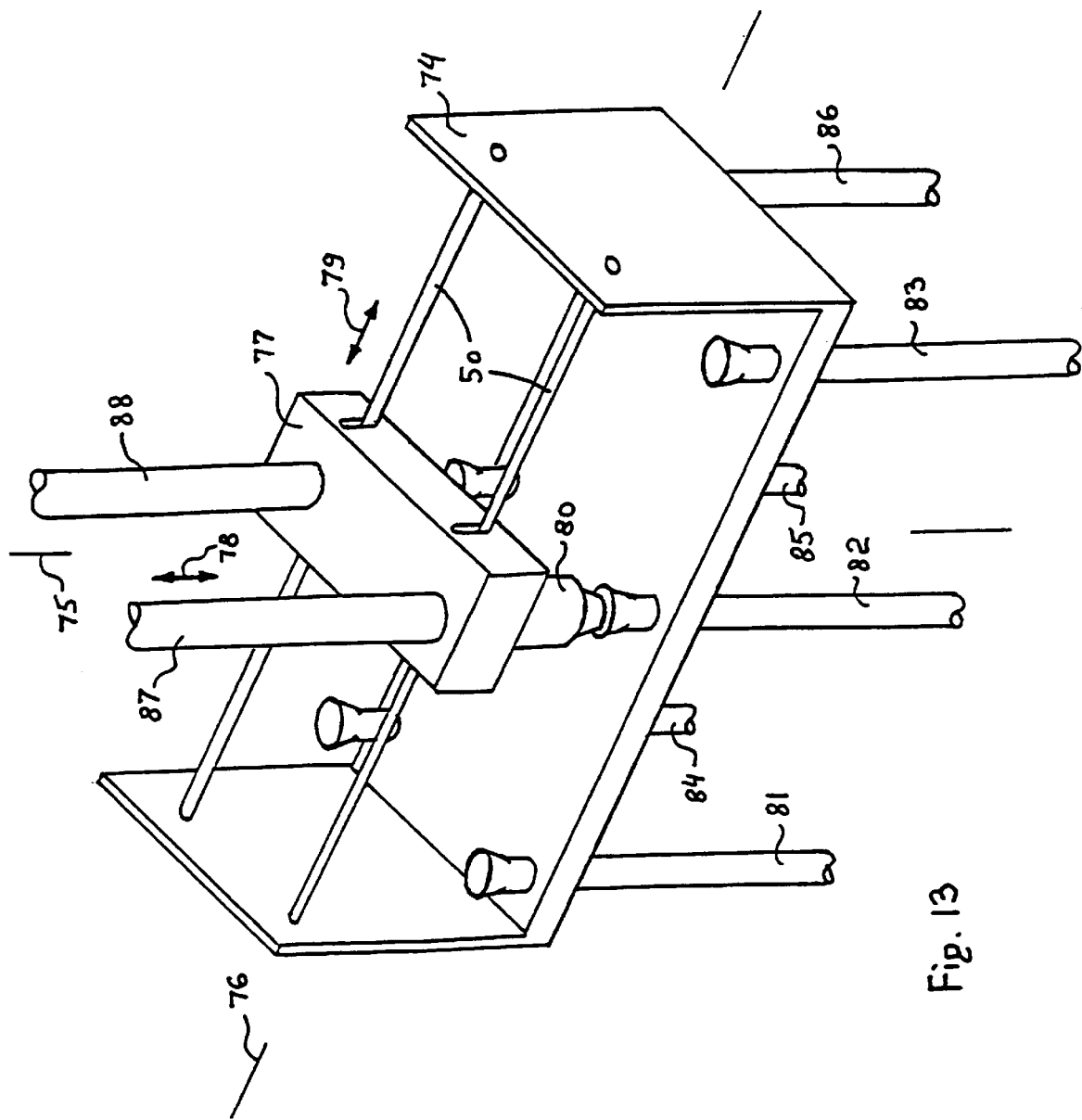
FIG. 13 is a simplified isometric spatial top view of the controllable valved means.
Figure 14:
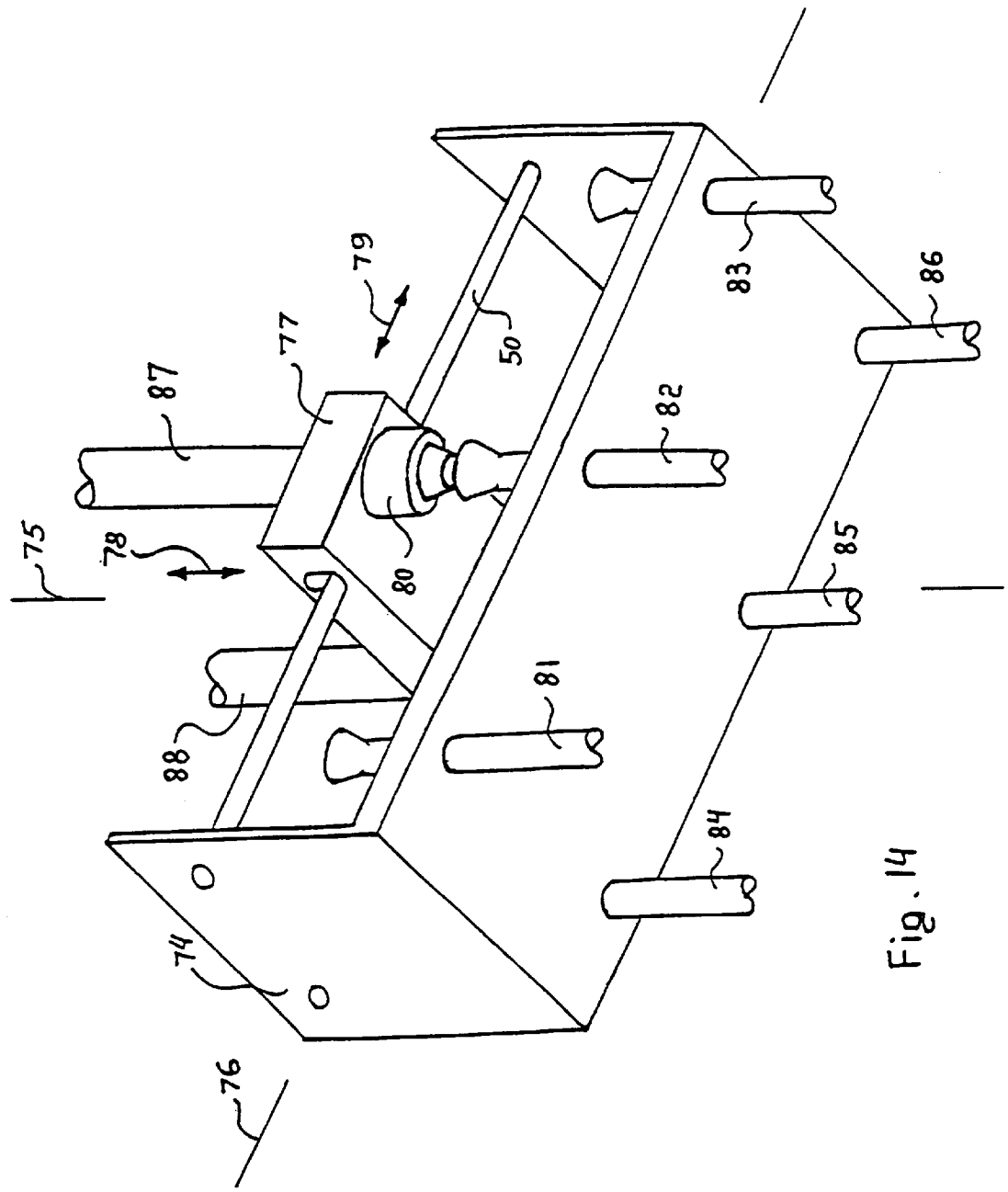
FIG. 14 is a simplified isometric spatial bottom view of the controllable valved means.

FIGS. 13, 14 represent the simplified spatial top and bottom views of the controllable valved means 74, where is shown the simplified construction of the mentioned above valved means 74 and the basic housing of the extended tubular means for N=3, referring to FIGS. 6, 7, 11.

An improved method and device operate as follow below. Referring to FIG. 12, an outside air by an entrance particle flow tubular means 46 and the controllable blowing means 22 through the controllable flow measuring means 23 by an extended entrance particle flow tubular means 12 flows to the controllable inlet valved means 33 of the valved means 74. The controllable inlet valved means 33 distributes an air flow (particle flow) to one of N=1, 2, . . . , i, . . . , m particle flow channels, depending on the particle size, which is intended for the counting and measuring. For example, the intended channel will be i-th. The particles flow by the appropriate extended inlet particle flow tubular means 54 through an i-th particle flow inlet filter 58 of an inlet filtrating means 48 and through a capillary inlet particle flow means 62 into particle detecting system 19. Each particle flow inlet filter 56–59 of the inlet filtrating means 48 is intended for one size particles only. It means, for example, if i-th channel is intended for counting and measuring 0.5 μm particles, the particle flow inlet filter 58 filtrates everything over 0.5 μm, providing a particle sorting for the further unobstructed passage of already predetermined size particles through an appropriate capillary particle flow means. The particle detecting system 19 processes assaying air, according an improved method, as follow below. The chosen capillary inlet particle flow means 62 has inside diameter intended especially for measuring and counting the chosen particles (for example, 0.5 μm).

The axis of each capillary inlet particle flow means is coincident with the axis of the appropriate capillary outlet particle flow means and intersects a light beam axis 2 on the device axis 1 at the point 8, which belongs to the first focus 8 of the mirror or optical system, depending on the use (see FIGS. 5–8,10,11). By improved method, all particles of the particle flow pass through the focal point (focus) 8. The scattered light reflected by mirror system or passed through optical system is detected by the detection means (not shown on FIGS. 5–14) at the second focus (not shown on FIGS. 5–14). The signals, related to the particles (for chosen example—0.5 μm), from detection means follow to the control system 21 for processing and indicating the results on the terminal means (not shown) of an improved device. The counted and measured particles through the appropriate capillary outlet particle flow means 66, extended outlet particle flow tubular means 70 flow to the controllable outlet valved means 44 of the valved means 74.

The outlet valved means 44 is synchronized with the inlet valved means 33, hereby providing the simultaneous connection of the appropriate inlet and outlet means of the chosen channel to the particle detecting system 19. The synchronization of the mentioned above inlet 33 and outlet 44 valved means can be provided by handle or electronic control. Further the counted and measured particles from the outlet valved means 44 by an extended exit particle flow tubular means 14 flow to the controllable purging means 20. The purging means 20 is synchronized with the blowing means 22, providing stable air (particle) flow through the particle detecting system 19. The air flow is measured by controllable flow measuring means 23, which is also controlled by a control system 21, and information about air flow characteristics is indicated by the terminal means of the control system 21.

The particle flow from the purging means 20 flows by an extended exit particle flow tubular means 14 to the outlet filtrating means 49. After filtration, the filtrated air flow by an exit particle flow tubular means 51 flows into the outside environment.

On FIGS. 13, 14 are also presented a controllable valved means 74 for N=3. A switching means 77 by the longitudinal, sliding along the directors 50 (in the directions 79 along an axis 76, for example, by handle shifting) provides the synchronous connection an inlet particle flow tubular means 87 of the valved means 74 and the outlet particle flow tubular means 88 of the valved means 74 to the appropriate inlet 81–83 (channels 30–32) and outlet 84–86 (channels 30–32) particle flow tubular means of the valved means 74. By the lateral shifting of the switching means 77 along an axis 75 (a direction 78—down) is provided the fixation of the mentioned above switching means 77 and non-leaking tight connection of the inlet 87 and outlet 88 particle flow tubular means with the appropriate pair 81–84 or 82–85 or 83–86 of the inlet 81–83 and outlet 84–86 particle flow tubular means., considering gaskets 80 and the ground-in conic exit mouths of the connecting tubular means of the valved means 74. For the automatic control, the valved means 74 comprises a transmission means (for example, a worm gear—not shown on FIGS. 13, 14, wherein by rotation of the directors 50 is provided the shifting of the switching means 77 along axis 76 with automatic fixation it along axis 75). The inlet 87 and outlet 88 particle flow tubular means can be presented by a plurality (N'=2, 3, . . . , i, . . . , m) of the inlet particle flow tubular means (not shown) and an appropriate plurality of outlet particle flow tubular means (not shown), and the valved means 74 can provide a synchronous connection of at least two channel inlet and outlet particle flow tubular means to extended entrance 12 and exit 14 particle flow tubular means respectively.

Referring again to FIG. 12, the N=1, 2, . . . , i . . . ,m inlet particle flow tubular means of the inlet valved means 33 (not shown on FIG. 12) are appropriately connected to the N=1, 2, . . . , i . . . ,m extended inlet particle flow tubular means 52–55 and N=1, 2, . . . , i, . . . ,m outlet particle flow tubular means of the outlet valved means 44 (not shown on FIG. 12) are appropriately connected to the N=1, 2, . . . , i, . . . , m extended outlet particle flow tubular means 68–71.

For assaying of the liquids (drinking water, for example), an improved device comprise an entire undivided capillary particle flow means, which can have, for example, the circle or square inside geometric form with inside dimensions adequate to the predetermined size particle and these inside dimensions can be correlated with the dimensions of the capillary inlet particle flow means, mentioned above. The capillary particle flow system, as a module of the particle detecting system, can be interchangeable to provide the analysis of other size particles.

Thus, by an improved method in an improved device each channel is intended for a priori determinate size of particles only, providing the precision of counting and measuring the particles.

CONCLUSION, RAMIFICATION AND SCOPE

Accordingly the reader will see that, according to the invention, I have provided a precise and effective method and device, which provide counting and measuring of all particles of the assayed air (gas) or liquid. An improved method and device provide authenticity of the real quantity and size of the particles in the assayed mixture of air or liquid, because all plurality of the scattered light is focused and considered. Also the improved method and device provide correctness of the resulting information, because the light noises (light background) inside an improved device is eliminated.

While the above description contains many specificities, these should not construed as limitations on the scope of the invention, but as exemplification of the presently-preferred embodiments thereof. Many other ramifications are possible within the teaching to the invention. For example, an improved method and device provide authentic counting and measuring the close particles sizes, using the same channel. For instance, if the particle flow channel is intended for counting and measuring 0.5 µm particles, this channel can also be used, for example, for counting and measuring 0.45 µm particles, 0.4 µm particles, because it will still eliminate the beside passage of two particles at the same moment of time inside chosen capillary particle flow means.

Thus, the scope of the invention should be determined by the appended claims and their legal equivalents, and not by examples given.

THE DRAWING REFERENCE NUMERALS WORKSHEET

1.—a device axis;
2.—a light beam axis;
3.—a particle flow axis;
4.—a mirror system;
5.—a light detector;
6.—a focused scattered light;
7.—an unfocused scattered light;
8.—a first focus;
9.—a second focus;
10.—a capillary inlet particle flow means;
11.—an optical system;
12.—an extended entrance particle flow tubular means;
13.—a capillary outlet particle flow means;
14.—an extended exit particle flow tubular means;
15.—a particle flow direction;
16.—a chamber of an optical system;
17.—an ellipsoidal mirror;
18.—a non-divergent quadric mirror;
19.—a particle detecting system;
20.—a purging means;
21.—a control system;
22.—a blowing means;
23.—a flow measuring means;
24.—a capillary inlet particle flow means of the first particle flow channel 30;
25.—a capillary inlet particle flow means of the second particle flow channel 31;
26.—a capillary inlet particle flow means of the third particle flow channel 32;
27.—a capillary outlet particle flow means of the first particle flow channel 30;
28.—a capillary outlet particle flow means of the second particle flow channel 31;
29.—a capillary outlet particle flow means of the third particle flow channel 32;
30.—a first particle flow channel;
31.—a second particle flow channel;
32.—a third particle flow channel;
33.—an inlet valved means of the valved means 74;
34.—an extended inlet particle flow tubular means of the first particle flow channel 30;
35.—an extended inlet particle flow tubular means of the second particle flow channel 31;
36.—an extended inlet particle flow tubular means of the third particle flow channel 32;
37.—an extended outlet particle flow tubular means of the first particle flow channel 30;
38.—an extended outlet particle flow tubular means of the second particle flow channel 31;
39.—an extended outlet particle flow tubular means of the third particle flow channel 32;
40.—a first channel inlet filter;
41.—a second channel inlet filter;
42.—a third channel inlet filter;
43.—an outlet particle flow means;
44.—an outlet valved means of the valved means 74;
45.—an outlet particle flow means axis;
46.—an entrance particle flow tubular means;
47.—a portion of the mirror surface;
48.—an inlet filtrating means;
49.—an outlet filtrating means;
50.—a director;
51.—an exit particle flow tubular means;
52.—an extended inlet particle flow tubular means of 1-st particle flow channel;
53.—an extended inlet particle flow tubular means of 2-nd particle flow channel;
54.—an extended inlet particle flow tubular means of i-th particle flow channel;
55.—an extended inlet particle flow tubular means of m-th particle flow channel;
56.—a 1-st particle flow channel inlet filter of the inlet filtrating means 48;
57.—a 2-nd particle flow channel inlet filter of the inlet filtrating means 48;
58.—an i-th particle flow channel inlet filter of the inlet filtrating means 48;
59.—a m-th particle flow channel inlet filter of the inlet filtrating means 48;
60.—a capillary inlet particle flow means of 1-st particle flow channel;
61.—a capillary inlet particle flow means of 2-nd particle flow channel;
62.—a capillary inlet particle flow means of i-th particle flow channel;
63.—a capillary inlet particle flow means of m-th particle flow channel;
64.—a capillary outlet particle flow means of 1-st particle flow channel;
65.—a capillary outlet particle flow means of 2-nd particle flow channel;
66.—a capillary outlet particle flow means of i-th particle flow channel;
67.—a capillary outlet particle flow means of m-th particle flow channel;
68.—an extended outlet particle flow tubular means of 1-st particle flow channel;
69.—an extended outlet particle flow tubular means of 2-nd particle flow channel;
70.—an extended outlet particle flow tubular means of i-th particle flow channel;
71.—an extended outlet particle flow tubular means of m-th particle flow channel;
72.—an exit mouth of the inlet particle flow ;
73.—a chamber of the mirror system 4;
74.—a valved means;
75.—a lateral axis of the valved means 74;
76.—a longitudinal axis of the valved means 74;
77.—a switching means;
78.—a lateral direction of the valved means 74 shifting;
79.—a longitidinal direction of the valved means 74 shifting;
80.—a gasket.;
81.—a first channel inlet particle flow tubular means of the valved means 74;
82.—a second channel inlet particle flow tubular means of the valved means 74;
83.—a third channel inlet particle flow tubular means of the valved means 74;
84.—a first channel outlet particle flow tubular means of the valved means 74;

85.—a second channel outlet particle flow tubular means of the valved means 74;

86.—a third channel outlet particle flow tubular means of the valved means 74;

87.—an inlet particle flow tubular means of the valved means 74;

88.—an outlet particle flow tubular means of the valved means 74.

What is claimed is:

1. A method for counting and measuring particles illuminated by a light beam, said method comprising the steps of:

providing a particle detecting system, having a particle monitoring region and including a capillary particle flow system, comprising a plurality of capillary particle flow channels formed by an adequate plurality of capillary particle flow means;

directing said light beam toward said particle monitoring region so that said particles are monitored in said particle detecting system;

providing each of said plurality of capillary particle flow means with an appropriate cross-sectional inside dimensions for a passage of an appropriate predetermined size particles;

providing an intersection of an axis of each of said plurality capillary particle flow means with an axis of said light beam at a point within said monitoring region; and sensing a light created by said intersection of said light beam with said particles flowing through at least one of said plurality of capillary particle flow means, and providing an output which is effectively indicative of the size of said particles.

2. The method of claim 1, wherein said particles are selected and sorted into the predetermined size particle flows by a particle inlet filtration.

3. A device for counting and measuring particles illuminated by a light beam, said device comprising:

a particle detecting system, having a particle monitoring region and including a capillary particle flow system, comprising a plurality of capillary particle flow channels formed by an adequate plurality of capillary particle flow means, each of which has an appropriate cross-sectional inside dimensions for a passage of an appropriate predetermined size particles through said particle monitoring region; wherein an axis of each of said plurality of capillary particle flow means intersect each other at a point within said particle monitoring region;

a light beam source providing a light beam through said particle monitoring region so that said particles are monitored in said detecting system; wherein an axis of said light beam intersects the axes of said plurality of capillary particle flow means at said point within said particle monitoring region; and a sensing means, including a light detection means, detecting a light created by said intersection of said light beam with said particles flowing through at least one of said plurality of capillary particle flow means, and providing an output which is effectively indicative of the size of said particles.

4. The device of claim 3, wherein said capillary particle flow system is interchangeable with the other adequate capillary particle flow systems intended for a passage of other size particles.

5. The device of claim 3, wherein each capillary particle flow means of said plurality of capillary particle flow means is divided into a capillary inlet particle flow means and a capillary outlet particle flow means, axes of which are coincident, and wherein the division of said capillary particle flow means is occurred in an area of said point within said particle monitoring region.

6. The device of claim 5, wherein the plurality of capillary outlet particle flow means further is presented by a singular outlet particle flow means.

7. The device of claim 3, wherein said device for counting and measuring particles further comprises:

an entrance particle flow tubular means, coupling a blowing means with an outside environment;

an extended entrance particle flow tubular means, coupling said blowing means with a valved means through a flow measuring means;

a plurality of inlet filters of an inlet filtrating means, each of which provides selection and sorting of said particles into an appropriate predetermined size particle flow;

a plurality of extended inlet particle flow tubular means, coupling said valved means with an appropriate plurality of capillary particle flow means through said plurality of inlet filtrating means;

a plurality of extended outlet particle flow tubular means, coupling said valved means with said appropriate plurality of capillary particle flow means directly;

an extended exit particle flow tubular means, coupling said valved means with an outlet filtrating means through a purging means;

an exit particle flow tubular means, coupling said outlet filtrating means with said outside environment; and a control system electrically connected to said blowing means, said flow measuring means, said valved means, said particle detecting system, and to said purging means.

8. The device of claim 7, wherein said blowing means operates synchronously with said purging means.

9. The device of claim 7, wherein said valved means comprises:

a standing means connected with a plurality of channel inlet particle flow tubular means and with an adequate plurality of channel outlet particle flow tubular means;

a switching means connected with an inlet particle flow tubular means and with an outlet particle flow tubular means; and at least one of a plurality of directors, bonding said standing means with said switching means.

10. The device of claim 9, wherein said switching means is shifted at an appropriate position for a subsequent synchronous connection of an appropriate channel inlet particle flow tubular means with said inlet particle flow tubular means and an appropriate channel outlet particle flow tubular means with said outlet particle flow tubular means, providing the passage of the appropriate predetermined size particles by the appropriate capillary particle flow means of the appropriate capillary particle flow channel through the particle monitoring region of the particle detecting system; wherein said subsequent synchronous connection is provided by a shifting of said switching means at a final connecting position.

11. The device of claim 9, wherein said standing means further is connected with said inlet particle flow tubular means and with said outlet particle flow tubular means, and said switching means further is connected with said plurality of channel inlet particle flow tubular means and with said plurality of channel inlet particle flow tubular means.

* * * * *

UNITED STATES PATENT AND TRADEMARK OFFICE
CERTIFICATE OF CORRECTION

PATENT NO. : 5,946,091
DATED : August 31, 1999
INVENTOR(S) : Aleksandr L. Yufa

It is certified that error appears in the above-identified patent and that said Letters Patent is hereby corrected as shown below:

Column 3, line 52, change "FIG. 11 is a simplified drawing of the third" to --FIG. 11 is a simplified drawing of the first--;

Column 4, line 23, change "compresses" to --comprises--;

Column 5, line 10, change " $T_{min} = +$ " to -- $T_{min} = +$ --;

Column 5, line 29, change "(means channels)" to --means (channels)--;

Column 7, line 67 (last line), change "longitudinal, sliding" to --longitudinal sliding--;

Column 8, line 37, change "device comprise" to --device can comprise--;

Column 11, line 49, change "providing a light beam through" to --providing said light beam through--;

Column 12, line 21, change "plurality of inlet filtrating means" to --plurality of inlet filters of said inlet filtrating means--;

Column 12, line 64 (last line), change "of channel inlet" to --of channel outlet--.

Signed and Sealed this

Ninth Day of May, 2000

Q. TODD DICKINSON

*Attest:*

*Attesting Officer*  *Director of Patents and Trademarks*